United States Patent
Kojima et al.

(10) Patent No.: US 11,719,606 B2
(45) Date of Patent: Aug. 8, 2023

(54) METHOD AND REAGENT FOR CLEARING BIOLOGICAL TISSUE

(71) Applicant: University Public Corporation Osaka, Osaka (JP)

(72) Inventors: Chie Kojima, Osaka (JP); Akikazu Matsumoto, Osaka (JP)

(73) Assignee: UNIVERSITY PUBLIC CORPORATION OSAKA, Osaka (JP)

( * ) Notice: Subject to any disclaimer, the term of this patent is extended or adjusted under 35 U.S.C. 154(b) by 482 days.

(21) Appl. No.: 16/628,595

(22) PCT Filed: Jul. 3, 2018

(86) PCT No.: PCT/JP2018/025239
§ 371 (c)(1),
(2) Date: Jan. 3, 2020

(87) PCT Pub. No.: WO2019/009300
PCT Pub. Date: Jan. 10, 2019

(65) Prior Publication Data
US 2020/0217761 A1 Jul. 9, 2020

(30) Foreign Application Priority Data
Jul. 6, 2017 (JP) ................. 2017-132787

(51) Int. Cl.
*G01N 1/30* (2006.01)
*C12N 11/04* (2006.01)
*C12N 11/08* (2020.01)
*G01N 33/48* (2006.01)

(52) U.S. Cl.
CPC ............... *G01N 1/30* (2013.01); *C12N 11/04* (2013.01); *C12N 11/08* (2013.01); *G01N 33/48* (2013.01)

(58) Field of Classification Search
CPC .......... C12N 11/04; C12N 11/08; G01N 1/28; G01N 1/30; G01N 33/48
See application file for complete search history.

(56) References Cited

U.S. PATENT DOCUMENTS

| | | | | |
|---|---|---|---|---|
| 5,324,445 A | * | 6/1994 | Langley | C11D 17/0039 510/393 |
| 6,171,522 B1 | * | 1/2001 | Michot | C07D 251/70 429/188 |
| 2009/0241800 A1 | * | 10/2009 | Kyota | C09D 7/41 106/400 |

FOREIGN PATENT DOCUMENTS

| | | |
|---|---|---|
| JP | 2015-49101 A | 3/2015 |
| JP | 2015-533210 A | 11/2015 |
| JP | 2016-538569 A | 12/2016 |
| WO | 2014/025392 A1 | 2/2014 |
| WO | 2015/030164 A1 | 3/2015 |
| WO | 2015/041755 A1 | 3/2015 |

OTHER PUBLICATIONS

K. Chung et al., Structural and molecular interrogation of intact biological systems. Nature 497(7449), 332-337 (2013).
R. Tomer et al., Advanced CLARITY for rapid and high-resolution imaging of intact tissues, Nature Protocols, 2014, 9(7), 1682-1697.
Y. Ono et al., Preprints (63rd SPSJ Kansai Annual Kobe Polymer Research Symposium), Jul. 14, 2017, F-15 "Optical Clearing of Tissues by Using Acrylamide-Sodium Styrenesulfonate Gel" (in Japanese).
Y. Ono et al., Preprints (12th Kansai-Block Meeting for Young Investigators, Japanese Society for Biomaterials), Aug. 31, 2017, O-19 "Tissue Clearing Using Acrylamide-Styrenesulfonate Gel with Various Rations" (in Japanese).
C. Kojima et al., Polymer Preprints, Japan (66th SPSJ Symposium on Macromolecules), Sep. 6, 2017, 66(2), 3V02 "Improvement of Optical Tissue Clearing Method by Using Copolymer Gels with Acrylamide and Sodium Styrenesulfonate" (in Japanese).
Y. Ono et al., PMF Preprints, Japan (26th SPSJ Polymer Material Forum), Nov. 1, 2017, 26, 1PA14 "Development of Rapid Optical Tissue Clearing Process Using Anionic Polyacrylamide Gels" (in Japanese).
Y. Ono et al., Polymer Preprints, Japan (67th SPSJ Annual Meeting), May 8, 2018, 67(1), 1H17 "Development of rapid tissue clearing process by using acrylamide-acrylic acid copolymer gels" (in Japanese).
H. Du et al., Experimental and Therapeutic Medicine, 16(3): 1567-1576 published online Jun. 29, 2018.

* cited by examiner

*Primary Examiner* — Blaine Lankford
(74) *Attorney, Agent, or Firm* — Stites & Harbison, PLLC; Mandy Wilson Decker

(57) ABSTRACT

The present invention provides a method for rapidly clearing a biological tissue. According to the present invention, provided is a method for clearing a biological tissue, including the steps of: infiltrating the biological tissue with water-soluble ethylenically unsaturated monomers before, during or after fixing the biological tissue with a fixative, wherein the water-soluble ethylenically unsaturated monomers include at least a water-soluble ethylenically unsaturated monomer having an ionically dissociable group; polymerizing the water-soluble ethylenically unsaturated monomers to form a hydrogel in the fixed biological tissue; and removing a lipid from the fixed biological tissue.

20 Claims, 8 Drawing Sheets

METHOD AND REAGENT FOR CLEARING BIOLOGICAL TISSUE

TECHNICAL FIELD

The present invention relates to a method for clearing a biological tissue and a reagent therefor.

BACKGROUND ART

Fluorescent imaging is used as a useful tool for observing phenomena in vivo or diagnosing diseases. Conventional techniques provide two-dimensional images of tissue samples from near the surfaces (such as thin tissue sections), whereas it is difficult to acquire three-dimensional images of tissue samples.

In general, biological tissues are mainly composed of proteins, lipids and nucleic acids, which substances have different refractive indices. This is because biological tissues have heterogeneous refractive indices and therefore light does not transmit through biological tissue samples. Consequently, the insides of biological tissue samples are invisible from the surfaces.

Thus, techniques for clearing a biological tissue have been developed by homogenizing the refractive index of the biological tissue to be close to that of proteins, which are the main constituents, thereby controlling light scattering in the tissue.

The "CLARITY" method developed by Chung et al. is a technique to clear a tissue by fixing proteins in a polyacrylamide hydrogel and then electrophoretically removing lipids, which are a main factor of light scattering and heterogenous refractive index, followed by replacement of the liquid in the tissue with a solution having a refractive index close to that of proteins (Non-Patent Document 1, Patent Document 1).

In the CLARITY method, electrophoresis can easily cause tissue damage. To solve the problem, techniques have been developed in which lipids are gradually removed by shaking, instead of by electrophoresis (Non-Patent Document 2, Patent Documents 1 and 2). However, the clearing techniques, while hardly causing tissue damage, require a longer time (2 to 3 weeks) for removing lipids by shaking.

CITATION LIST

Patent Literature

Patent Document 1: Japanese Patent KOHYO Publication No. 2016-538569
Patent Document 2: Japanese Patent KOHYO Publication No. 2015-533210

Non-Patent Literature

Non-Patent Document 1: K. Chung et al., Nature, 497 (7449), 332-337 (2013)
Non-Patent Document 2: R. Tomer et al., Nature Protocols, 9 (7), 1682-1697 (2014)

SUMMARY OF INVENTION

Technical Problems

There is still a need for a technique that can rapidly clear a tissue while avoiding tissue damage.

Solution to Problems

With the foregoing in view, the present invention provides a method for clearing a biological tissue, the method including the steps of: (1) infiltrating the biological tissue with water-soluble ethylenically unsaturated monomers before, during or after fixing the biological tissue with a fixative, wherein the water-soluble ethylenically unsaturated monomers includes at least a water-soluble ethylenically unsaturated monomer having an ionically dissociable group; (2) polymerizing the water-soluble ethylenically unsaturated monomers to form a hydrogel in the fixed biological tissue; and (3) removing a lipid from the fixed biological tissue.

The present invention also provides a method for preparing a hydrogel having a cleared biological tissue embedded therein, the method including applying the above-mentioned clearing method to a biological tissue.

The present invention also provides use of a water-soluble ethylenically unsaturated monomer having an ionically dissociable group for clearing a biological tissue or preparing a hydrogel having a cleared biological tissue embedded therein.

The present invention further provides a reagent for clearing a biological tissue, the reagent including a water-soluble ethylenically unsaturated monomer having an ionically dissociable group.

Advantageous Effects of Invention

The present invention makes it possible to render a biological tissue transparent in a shorter time than by conventional methods, while avoiding tissue damage.

DESCRIPTION OF EMBODIMENTS

<Biological Tissue-Clearing Method>

Figure 1:
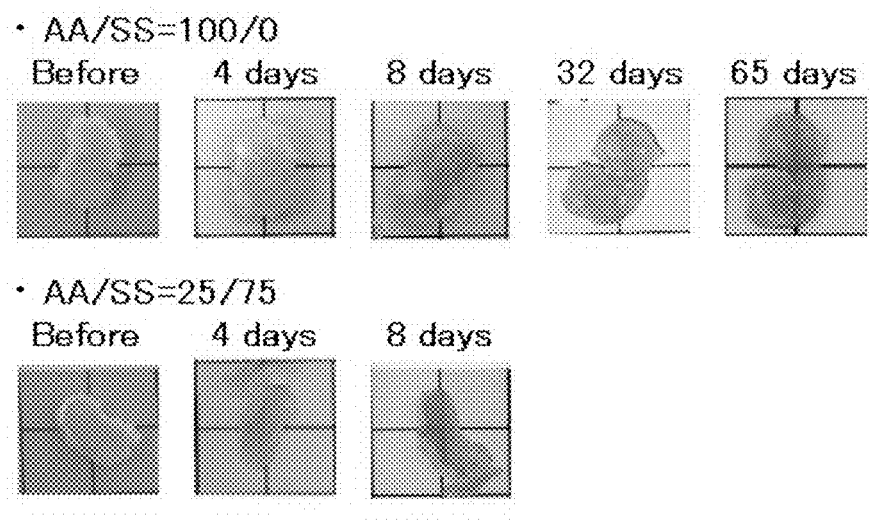
FIG. 1 illustrates photographs of biological tissue (cancer tissue) samples subjected to a conventional clearing method or one embodiment of the clearing method of the invention using sodium styrenesulfonate. In either method, lipids were removed by passive diffusion. The biological tissue samples are each placed on a grid board.

The method for clearing a biological tissue of the present invention is characterized by including the steps of: (1) infiltrating the biological tissue with water-soluble ethylenically unsaturated monomers before, during or after fixing the biological tissue with a fixative, wherein the water-soluble ethylenically unsaturated monomers include at least a water-soluble ethylenically unsaturated monomer having an ionically dissociable group; (2) polymerizing the water-soluble ethylenically unsaturated monomers to form a hydrogel in the fixed biological tissue; and (3) removing a lipid from the fixed biological tissue.

The present invention is based on the finding that, as demonstrated in Examples below, the use of a monomer unit having an ionically dissociable group to form a hydrogel shortens the time for delipidating (or clearing) a tissue by passive diffusion.

As used herein, "clearing" a biological tissue refers to an increased transmission through the biological tissue of light having at least a certain wavelength range (such as visible light or a part thereof, ultraviolet light, or infrared light), as compared to prior to the clearing.

The "biological tissue" is any tissue/organ of biological origin and may be a whole tissue/organ or a part thereof. The tissue is a biopsy or autopsy tissue, and may be a healthy tissue or a tissue with a (histochemical, biochemical or morphological, for example) abnormality or change caused by or causing a disease. The organism from which the tissue/organ derives is not particularly limited and is preferably an animal such as a mammal, bird, fish, amphibia or reptile and particularly preferably a mammal. The tissue may be stained/labeled with a fluorescent antibody or the like before or after being subjected to the clearing method of the invention.

The biological tissue may be a brain tissue (a whole brain, or a block or slice of brain) or any other tissue/organ.

(1) Infiltration Step

In this step, the biological tissue is infiltrated with the water-soluble ethylenically unsaturated monomers (hereinafter simply referred to also as "the monomers").

The water-soluble ethylenically unsaturated monomers to be infiltrated into the tissue include at least a water-soluble ethylenically unsaturated monomer having an ionically dissociable group. The "ionically dissociable group" may be an anionically dissociable group or a cationically dissociable group, and is preferably an anionically dissociable group. In the context of the present invention, the "anionically dissociable group" and the "cationically dissociable group" generate an anion and an cation, respectively, on the monomer in water.

The anionically dissociable group is any group capable of dissociating into an anion in water, and may be, for example, a sulfonate, carboxyl or phosphate group and is preferably a sulfonate or carboxyl group.

Specific examples of the monomer having a sulfonate group include styrenesulfonic acid, (meth)acryloxybenzenesulfonic acid, 2-(meth)acrylamido-2-methylpropanesulfonic acid, 2-(meth)acrylamidopropanesulfonic acid, 3-(meth)acrylamido-2-hydroxypropanesulfonic acid, 3-(meth)acryloxy-1-propanesulfonic acid, t-butylacrylamidosulfonic acid, (meth)allylsulfonic acid, (meth)allyloxybenzenesulfonic acid, vinylsulfonic acid, methylvinylsulfonic acid, sulfopropyl (meth)acrylate, (meth)acryloxyethylsulfonic acid, 2-hydroxy-3-(meth)acryloxypropylsulfonic acid, 2-(meth)acryloylamino-2,2-dimethylethanesulfonic acid, butyl (meth)acrylate-4-sulfonic acid and salts thereof, and the like. Among them, preferred are styrenesulfonic acid, (meth)acryloxybenzenesulfonic acid, 2-(meth)acrylamido-2-methylpropanesulfonic acid, 2-(meth)acrylamidopropanesulfonic acid, 3-(meth)acrylamido-2-hydroxypropanesulfonic acid, 3-(meth)acryloxy-1-propanesulfonic acid, vinylsulfonic acid and salts thereof.

Specific examples of the monomer having a carboxyl group include (meth)acrylic acid, itaconic acid, maleic acid, fumaric acid and salts thereof, and the like.

Specific examples of the monomer having a phosphate group include vinylphosphonic acid, methacryloxyethyl phosphate and salts thereof, and the like.

A salt of the anionically dissociable group may be an alkali metal salt (such as a sodium salt or a potassium salt), an alkaline earth metal salt (such as a calcium salt or a magnesium salt), an ammonium salt, or the like.

The cationically dissociable group is any group capable of dissociating into a cation in water and may be, for example, an amino group or a quaternary ammonium group.

Specific examples of the monomer having a cationically dissociable group include diethylaminoethyl (meth)acrylate, dimethylaminoethyl (meth)acrylate, diethylaminomethyl (meth)acrylate and salts thereof, and the like.

A salt of the cationically dissociable group may be a hydrochloric, sulfuric, carboxylic or phosphoric acid salt, or the like.

The monomer to be infiltrated into the tissue may include a water-soluble ethylenically unsaturated monomer other than the monomer having an ionically dissociable group. Such a further monomer is any monomer that is electrically neutral in an aqueous solution and may preferably be a monomer having an amino group (particularly, primary amino group) and may be, for example, a (meth)acrylamide-based monomer.

Specific examples of the (meth)acrylamide-based monomer may include N-vinylacetamide, (meth)acrylamide, N-methyl(meth)acrylamide, N-ethyl(meth)acrylamide, N-isopropyl(meth)acrylamide, N-n-propyl(meth)acrylamide, N-methyl-N-ethyl(meth)acrylamide, N,N-dimethyl (meth)acrylamide, N,N-ethylmethyl(meth)acrylamide, N,N-diethyl(meth)acrylamide and the like. Among them, (meth)acrylamide is preferred.

The proportion of the monomer having an ionically dissociable group to the total monomers is not particularly limited as long as the time for tissue delipidation can be reduced relative to that in a (conventional) method without using the monomer having an ionically dissociable group, and is preferably at least 50% by mole, more preferably at least 60% by mole, and more preferably at least 70% by mole.

The upper limit of the proportion of the monomer having an ionically dissociable group to the total monomers is not particularly limited as long as the formed hydrogel is rigid enough to maintain the structure of the delipidated biological tissue, and may be 100% by mole and for example 99% by mole, 95% by mole, 90% by mole or 85% by mole.

Thus, the water-soluble ethylenically unsaturated monomers may include 50 to 100% by mole of the water-soluble ethylenically unsaturated monomer having an ionically dissociable group and 0 to 50% by mole of such a further monomer as described above.

The water-soluble ethylenically unsaturated monomers are infiltrated into the biological tissue by contacting a solution of the monomers with the biological tissue (hereinafter, the solution of the water-soluble ethylenically unsaturated monomers is simply referred to also as "the monomer solution").

A solvent used in the monomer solution may be saline or a buffered saline. The buffer solution may be appropriately selected from those known in the art, and may be, for example, a phosphate buffer solution, a borate buffer solution, a Tris-hydrochloride buffer solution, a citrate buffer solution, a carbonate buffer solution, a succinate buffer solution, an acetate buffer solution or the like (for example, 0.01 to 1 M [preferably 0.01 to 0.1 M] and pH 6 to 10 [preferably pH 7 to 9]). The buffer solution may contain, as required, NaCl, a surfactant (see below) and/or a preservative (such as sodium azide). Specific examples of the buffer solution include PBS, PBS-T, BB and BB-T. Particularly if the infiltration step is carried out by a method other than perfusion, the monomer solution preferably contains a non-ionic surfactant (see below; such as Tween 20, Triton X-100 or saponin).

The concentration (mass/volume) of the monomers in the solution is not particularly limited, and may be, for example, 0.5% to 10%, 1% to 8% or 2% to 6%.

In order to prevent initiation of the polymerization reaction, it is preferable that the solution is prepared at a low temperature (such as a temperature of 0 to 5° C.) (for example, on ice) and the prepared solution is stored at a low temperature.

The monomer solution may contain a crosslinking agent. Examples of the crosslinking agent include N,N'-methylenebisacrylamide, ethylene glycol di(meth)acrylate, polyethylene glycol di(meth)acrylate, propylene glycol di(meth)acrylate, polypropylene glycol di(meth)acrylate, allyl methacrylate, trimethylolpropane di(meth)acrylate, trimethylolpropane tri(meth)acrylate, pentaerythritol di(meth)acrylate, pentaerythritol tri(meth)acrylate, pentaerythritol tetra(meth)acrylate, trimethylolpropane diallyl ether, pentaerythritol triallyl ether, divinylbenzene, bisphenol di(meth)acrylate, isocyanurate di(meth)acrylate, tetraallyloxyethane, triallylamine, polyethylene glycol di(β-acryloyloxy propionate), trimethylolpropane tri(β-acryloyloxy propionate), poly(meth)allyloxyalkanes and the like. Among them, N,N'-methylenebisacrylamide and allyl methacrylate are preferred and N,N'-methylenebisacrylamide is more preferred.

The crosslinking agent may be used, for example at 0.1 to 10 parts by mass, preferably 0.5 to 5 parts by mass, and more preferably 1 to 2 parts by mass, with respect to 100 parts by mass of the monomers. Alternatively, the crosslinking agent may be used at a concentration (mass/volume) of, for example, 0.01 to 0.5%, and preferably 0.02 to 0.3% in the monomer solution.

The monomer solution may contain a polymerization initiator for efficient polymerization reaction.

The polymerization initiator may be a known one (for example, a thermal polymerization initiator or a photopolymerization initiator), and is preferably a thermal polymerization initiator, and more preferably an azo polymerization initiator.

Specific examples of the polymerization initiator include 2,2'-azobis(isobutyronitrile), 2,2'-azobis(2-methylbutyronitrile), 2,2'-azobis(2,4-dimethylvaleronitrile), 2,2'-azobis(4-methoxy-2, 4-dimethylvaleronitrile), 1, 1'-azobis(cyclohexane-1-carbonitrile), 2,2'-azobis[2-(2-imidazolin-2-yl)propane]dihydrochloride, 2,2'-azobis[2-(2-imidazolin-2-yl)propane]disulfate dihydrate, 2,2'-azobis[2-(2-imidazolin-2-yl)propane], 2,2'-azobis[2-(5-methyl-2-imidazolin-2-yl)propane]dihydrochloride, 2,2'-azobis[2-[1-(2-hydroxyethyl)-2-imidazolin-2-yl]propane]dihydrochloride, 2,2'-azobis[N-(2-carboxyethyl)-2-methyl] hydrate, 2,2'-azobis[N-(2-carboxyethyl)-2-methylpropionamidine] n-hydrate, ammonium persulfate, di-tert-butyl peroxide, tert-butyl hydroperoxide, benzoyl peroxide and the like. The polymerization initiator is preferably 2,2'-azobis[2-(2-imidazolin-2-yl)propane]dihydrochloride, 2,2'-azobisisobutyronitrile or ammonium persulfate, and more preferably 2,2'-azo bis [2-(2-imidazolin-2-yl)propane]dihydro chloride.

The polymerization initiator may be, for example at 10 to 60 parts by mass, and preferably 20 to 40 parts by mass, relative to 100 parts by mass of the monomers. Alternatively, the polymerization initiator may be used in the monomer solution at a concentration (mass/volume) of, for example, 0.01 to 1%, preferably 0.05 to 0.5%, and more preferably 0.1 to 0.5%.

The infiltration is carried out in any way to allow the monomer solution to contact with the biological tissue. For example, infiltration may be carried out by applying the monomer solution to the biological tissue, or infusing or immersing the biological tissue with/in the monomer solution.

Alternatively, the biological tissue may be infiltrated with the monomer solution by perfusion (such as cardiac perfusion). The perfusion rate may be, for example, 10 to 100 ml/min according to the animal's size. If infiltration is by perfusion, the biological tissue of interest removed from the animal may be further infiltrated by immersion.

The contact time may be appropriately determined by taking into account the size of the biological tissue and the tissue penetrance of the monomer solution, and may be, for example, 15 minutes or more, 30 minutes or more, 1 hour or more, 6 hours or more, 12 hours or more, 1 day or more, 2 days or more or 3 days or more. The upper limit is not particularly limited, and may be, for example, 1 week at maximum.

The temperature of the monomer solution upon contact/infiltration may be a temperature of, for example, 0 to 10° C., preferably 2 to 8° C., and preferably 2 to 5° C. If the infiltration is not by immersion, it is preferable to maintain the biological tissue itself at a low temperature (such as a temperature of 0 to 5° C.).

The infiltration step may be performed before, during and/or after fixing the biological tissue.

The biological tissue may be fixed with a commonly used fixative. Examples of the fixative include formaldehyde, paraformaldehyde, glutaraldehyde and the like. Among them, paraformaldehyde is preferred. The fixative concentration used (volume/volume) is not particularly limited, and may be generally 50% or less, such as 1% to 40%, preferably 1% to 20%, more preferably 1% to 10%, and more preferably 1% to 5%.

If the infiltration step is carried out during the fixation, the monomer solution may contain the fixative. In this case, the fixed biological tissue may be allowed to further contact with the monomer solution (preferably by immersion), which may or may not contain the fixative.

(2) Polymerization Step

In this step, the monomers are polymerized to form a hydrogel in the fixed biological tissue.

The polymerization may be carried out by heat and/or by radiation. Heat and/or radiation conditions are any conditions under which the monomers in the biological tissue can be polymerized to form a hydrogel, and may be appropriately selected from known conditions. For example (particularly if a thermal polymerization initiator is used), the polymerization in the biological tissue may be carried out by placing the biological tissue (preferably in the monomer solution) in a thermostatic oven or a warm water bath.

The temperature may be a temperature of, for example, 25 to 60° C., preferably 30 to 50° C., and more preferably 35 to 40° C.

The polymerization time is not particularly limited and is a time enough to complete the hydrogel formation by the polymerization reaction, and is usually 15 minutes to 48 hours, such as 1 hour to 48 hours, preferably 2 hours to 36 hours, and more preferably 3 hours to 24 hours.

In order to facilitate the polymerization, inert gas (such as nitrogen) may be fed into the monomer solution to remove oxygen (which may inhibit polymerization) therefrom prior to the polymerization step, particularly if it is carried out while the biological tissue is in the monomer solution. Alternatively, oxygen may be removed under vacuum or reduced pressure from the monomer solution and the biological tissue before the polymerization step, and additionally the polymerization may be carried out in an inert gas atmosphere. The monomer solution may be shaken during the polymerization step. Dissolved oxygen in the monomer solution may be removed prior to the infiltration step.

(3) Lipid Removal Step

In this step, lipids are mainly removed from the biological tissue.

Lipids are present in biological tissues at relatively high amounts and have refractive indices different from those of proteins, and insoluble lipids scatter light. Therefore, delipidation reduces light scattering and homogenizes refractive indices within the biological tissue (or approximates to the refractive indices of proteins), thereby rendering the biological tissue transparent. Accordingly, the present step may be also referred to as "clearing step". In addition to lipids, any other constituents (but not proteins) may also be removed from the biological tissue during the present step.

Prior to the delipidation, excess hydrogel may be removed from the biological tissue.

Lipids are removed with a surfactant. The surfactant may be used in a solution of, for example, 0.5 to 30%, preferably 1 to 15%, more preferably 2 to 10%, and more preferably 2 to 8% (mass/volume). The surfactant may be dissolved in a buffer solution. The buffer solution used may be any one of those mentioned above, and is preferably a borate buffer solution having a bactericidal activity. The buffer solution preferably has a pH of 7 to 9. Specific examples of the buffer solution may include 0.1 to 1 M borate buffer solutions (pH 8 to 9) and 0.01 to 0.1 M PBS (pH 7.4 to 8.5).

The surfactant may be ionic or nonionic, and preferably is an ionic surfactant, and more preferably an anionic surfactant.

Examples of the nonionic surfactant include saponin, digitonin, polyoxyethylene sorbitan monooleate, polyoxyethylene sorbitan monolaurate, polyoxyethylene sorbitan monopalmitate, polyoxyethylene sorbitan monostearate, polyvinyl alcohol, polyoxyethylene octyl phenyl ether and the like.

Examples of the anionic surfactant include sodium alkyl sulfate (such as sodium lauryl sulfate), sodium alkyl sulfonate, sodium polyoxyethylene alkyl ether sulfate, bile salt (such as sodium cholate and sodium deoxycholate), N-laurylsarcosine and the like. Among them, sodium lauryl sulfate is preferred.

Examples of the cationic surfactant include alkyl quaternary ammonium and the like. Examples of the amphoteric surfactant include 2-alkyl-N-carboxymethyl-N-hydroxyethyl imidazolium betaine, 3-[(3-cholamidopropyl)dimethylammonio]-1-propanesulfonate (CHAPS) and the like.

Delipidation may be by passive diffusion, for example. The "passive diffusion" as used herein refers to diffusion of substances without using a technique, such as electrophoresis, that actively (or forcibly) moves the substances. Specifically, passive diffusion may be carried out by, for example, incubating the biological tissue in a buffer solution (for example, 0.01 to 1 M and pH 6 to 10) containing a surfactant (preferably while shaking). The incubation temperature may be, for example, room temperature or a temperature of 25 to 50° C., preferably 30 to 50° C., and more preferably 35 to 45° C. The incubation time may be appropriately determined according to the size of the biological tissue. The incubation time can be reduced from, for example, 2 weeks or more in a conventional method to, for example, 12 days or less, preferably 10 days or less, more preferably 8 days or less, and more preferably 7 days or less in a method of the present invention. Thus, the incubation time may be, for example 4 to 12 days, particularly 3 to 12 days, more particularly 2 to 12 days, and still more particularly 1 to 12 days.

Alternatively, delipidation may be by electrophoresis using an ionic surfactant (preferably an anionic surfactant, particularly sodium lauryl sulfate).

The electrophoresis is carried out with, for example, a DC voltage of 10 to 60 V at a temperature of 20 to 60° C. The run time can be reduced from 3 to 5 days in a conventional method, to for example 2 hours to 3 days, and preferably 12 hours to 2 days in the method of the present invention. Thus, electrophoretic delipidation according to the method of the present invention can reduce tissue damage.

Prior to the electrophoresis, the biological tissue may be washed once or more times (such as 2 or 3 times) with a buffer solution containing the ionic surfactant used in the electrophoresis, to remove the residual fixative and/or unreacted monomers.

During the lipid removal step, the buffer solution containing the surfactant may be replaced as needed (such as every 12 to 24 hours) or constantly with a fresh one.

If using an ionic surfactant in the lipid removal step, the biological tissue is preferably further incubated with a nonionic surfactant to remove the ionic surfactant. In this case, the concentration (volume/volume) of the nonionic surfactant may be, for example, 0.01 to 1%. Specific examples of a buffer solution containing a nonionic surfactant include BB-T and PBS-T. If using a nonionic surfactant in the lipid removal step or if carrying out an incubation with a nonionic surfactant after the lipid removal step, the biological tissue may be incubated with a buffer solution devoid of any surfactant to remove the nonionic surfactant. The incubation conditions may be, for example, at a temperature of 30 to 40° C. for 12 hours to 2 days. Incubation may be carried out while shaking.

(4) Further Clearing Step

Clearing a biological tissue may be achieved by removing lipids from the biological tissue. However, for further clearing, the solvent (mostly, water used as a solvent in the buffer solutions and others) in the biological tissue may be replaced with a solution having a refractive index identical to, or approximating, that of the delipidated biological tissue (in most cases, a refractive index approximating that of proteins [1.4 to 1.5, particularly, 1.45 to 1.5]) (which solution is hereinafter referred to also as "refractive index homogenizing solution" or "refractive index matching solution"). Example of such a substance include ethylene glycol, polyethylene glycol (such as a 90% PEG400 solution), glycerol (such as 20 to 90% glycerol solutions, mixed solutions of 75% glycerol and 20 to 40% glucose), sucrose (such as a 75% sucrose solution), fructose, polyvinylpyrrolidone, FocusClear® (CelExplorer Labs Co.), 80 to 90% (mass/volume) of Histodenz (Sigma Aldrich) and the like.

The replacement may be carried out by, for example, incubating the biological tissue in any one of the solutions as mentioned above at a temperature of 30 to 40° C. The incubation time is a time enough to further clear the biological tissue as desired, and may be, for example, 10 minutes to 3 days (according to the size of the tissue).

The cleared biological tissue may be stored in a buffer solution (preferably containing a preservative).

<Biological Tissue-Clearing Reagent/Kit>

The biological tissue-clearing reagent of the present invention is characterized in that the reagent includes a water-soluble ethylenically unsaturated monomer having an ionically dissociable group.

The monomer having an ionically dissociable group is as described in the section <Biological tissue-clearing method> above.

The present reagent may further include a water-soluble ethylenically unsaturated monomer other than the monomer having an ionically dissociable group. The further monomer may be as described in the section <Biological tissue-clearing method> above. In one specific embodiment, the present reagent includes the monomer having an ionically dissociable group and a (meth)acrylamide-based monomer.

The present reagent may further include a crosslinking agent and/or a polymerization initiator. The crosslinking agent and the polymerization initiator may be as described in the section <Biological tissue-clearing method> above. In one specific embodiment, the present reagent includes the monomer having an ionically dissociable group, a (meth) acrylamide-based monomer and a crosslinking agent and/or a polymerization initiator. In one particular embodiment, the present reagent includes a monomer of styrenesulfonic acid or a salt thereof, an acrylamide monomer and methylenebisacrylamide.

The present reagent may include the monomer having an ionically dissociable group and the further monomer and optionally a crosslinking agent and/or a polymerization initiator in amounts to achieve the ratio described in the section <Biological tissue-clearing method> above.

The present reagent may be provided as a frozen solution.

If the present reagent includes the monomer having an ionically dissociable group, the further monomer and optionally a crosslinking agent and/or a polymerization initiator, they may be each provided in separate containers (this embodiment may be referred to as "(reagent) kit").

The reagent/kit of the present invention may include a buffer solution for dissolving the monomers and others. The buffer solution may be as described in the section <Biological tissue-clearing method> above.

The reagent/kit of the present invention may include a protein fixative. The fixative may be as described in the section <Biological tissue-clearing method> above.

The reagent/kit of the present invention may include a refractive index-matching solution. The solution may be as described in the section <Biological tissue-clearing method> above.

The biological tissue-clearing reagent of the present invention is suitably used in the biological tissue-clearing method described above.

<Tissue-Embedding Hydrogel Preparation Method>

The preparation method of the present invention is characterized in that the biological tissue-clearing method described above is applied to a biological tissue. According to the present preparation method, a cleared biological tissue may be prepared in a shorter time than a conventional method, and particularly if the lipid removal step is carried out by passive diffusion, tissue damage can be avoided and the cost may be reduced.

The biological tissue prepared according to the present method may be used as a specimen for research and educational purposes, or for promoting the present tissue-clearing method or reagent.

EXAMPLES

Reagents

The following reagents were used in the present Examples: paraformaldehyde (Nacalai Tesque, Inc.) as a protein fixative; acrylamide (AA; Nacalai Tesque, Inc.), sodium p-styrenesulfonate (SS; Tokyo Kasei Kogyo Co., Ltd.), sodium 2-acrylamido-2-methylpropane sulfonate (AMPS; Sigma Aldrich) and acrylic acid (AcA; Nacalai Tesque, Inc.) as monomers; N,N'-methylenebisacrylamide (bisAA; Tokyo Kasei Kogyo Co., Ltd.) as a crosslinking agent; 2,2'-azobis [2-(2-imidazolin-2-yl)propane]dihydrochloride (VA-044; Wako Pure Chemical Industries, Ltd.) as a low-temperature type water-soluble polymerization initiator; sodium chloride, disodium hydrogen phosphate, potassium dihydrogen phosphate and potassium chloride (all Wako Pure Chemical Industries, Ltd.) as reagents in 10×PBS solution; sodium lauryl sulfate (Nacalai Tesque, Inc.) as a surfactant in a delipidating solution; boric acid (Nacalai Tesque, Inc.) as a bactericide in the delipidating solution; ethylene glycol (Nacalai Tesque, Inc.) as a refractive index homogenizing solution; Triton X-100 (Tokyo Kasei Kogyo Co., Ltd.) as a reagent for removing the ionic surfactant; and polyoxyethylene sorbitan monolaurate (Tween20; Nacalai Tesque, Inc.) and Monoclonal Anti-Actin, α-Smooth Muscle-FITC antibody produced in mouse, clone 1A4 (Sigma-Aldrich) as immunostaining reagents.

Biological Tissue Clearing (1)
Clearing Procedures
1. Preparation of Monomer Solutions Monomer solutions containing a fixative were prepared as follows.

Monomers (2.0 g, final concentration: 4.0 wt/vol %) at a molar ratio of AA/SS=100/0 or 25/75, bisAA (final concentration: 0.050 wt/vol %), a polymerization initiator (VA-044; final concentration: 0.25 wt/vol %) and paraformaldehyde (final concentration: 4.0 wt/vol %) were dissolved in 50 ml of 1×PBS solution (pH 7.4).

2. Penetration of Monomers into Biological Tissue ("Infiltration Step")

In 50-ml conical tubes, biological tissue samples (cancer tissues; 1 cm×1.5 cm×0.5 cm) were immersed in the respective monomer solutions at 4° C. for 1 day, thereby allowing the monomer solutions to penetrate into the biological tissue samples.

3. Polymerization of Monomers ("Polymerization Step")

The conical tubes were placed in a thermostatic oven at 37° C., thereby initiating polymerization reaction of the monomers infiltrated into the biological tissues. The polymerization reaction was carried out for 24 hours.

4. Delipidation ("Lipid Removal Step" or "Clearing Step")

Each of the biological tissue samples was incubated in 30 ml of a 0.8 M borate buffer solution (pH 8.5) containing 4% (wt/vol) sodium lauryl sulfate at 37° C. while shaking using an incubator (BIO-CHAMBER BCP 120-F; Taitec Corporation) and a small rotary shaker (NR-2; Taitec Corporation).

5. Removal of Surfactant

Each of the biological tissue samples was incubated in 30 ml of a 0.1 M borate buffer solution (pH 8.5) containing 0.1% by volume of Triton X-100 at 37° C. while shaking for 1 day.

6. Replacement of Solvent in Tissue (with Refractive Index-Homogenizing Solution)

Each of the biological tissue samples was incubated in ethylene glycol at room temperature for 1 hour.

Results

FIG. 1 shows the biological tissue samples before and during the delipidation (after 4 and 8 days of incubation, and for AA/SS=100/0 only, also after 32 and 65 days of incubation), and after the solvent replacement. In the figure, the biological tissue samples are each placed on a 1-cm grid board.

As is clearly seen from the figure, the biological tissue samples were opaque before the delipidation regardless of the monomer solutions used. However, the biological tissue sample in which hydrogel had been formed from the monomers at a molar ratio of AA/SS=25/75 became transparent after 8 days of delipidation. Meanwhile, the biological tissue sample in which hydrogel had been formed from the monomers at a molar ratio of AA/SS=100/0 was still opaque even after 32 days of delipidation.

The biological tissue sample in which hydrogel had been formed from the monomers at a molar ratio of AA/SS=25/75 became completely transparent after 8 days of delipidation, followed by replacement of the solvent in the tissue with ethylene glycol.

Biological Tissue Clearing (2)
Clearing Procedures
1. Preparation of Monomer Solutions Monomer solutions containing a fixative were prepared as follows.

Monomers (0.4 g, final concentration: 4.0 wt/vol %) at a molar ratio of AA/SS=100/0 or 20/80, bisAA (final concentration: 0.050 wt/vol %), a polymerization initiator (VA-044; final concentration: 0.25 wt/vol %) and paraformaldehyde (final concentration: 4.0 wt/vol %) were dissolved in 10 mL of 1×PBS solution (pH 7.4).

2. Penetration of Monomers into Biological Tissue ("Infiltration Step")

In 50-ml conical tubes, biological tissue samples (cancer tissues; approximately 0.5 cm×0.5 cm×0.075 cm) were immersed in the respective monomer solutions at 4° C. for 1 day, thereby allowing the monomer solutions to penetrate into the biological tissue samples.

3. Polymerization of Monomers ("Polymerization Step")

The conical tubes were placed in a thermostatic oven at 37° C., thereby initiating polymerization reaction of the monomers infiltrated into the biological tissue samples. The polymerization reaction was carried out for 24 hours.

4. Delipidation ("Lipid Removal Step" or "Clearing Step")

Each of the biological tissue samples was incubated in 30 ml of a 0.8 M borate buffer solution (pH 8.5) containing 4% (wt/vol) sodium lauryl sulfate at 37° C. while shaking using an incubator (BIO-CHAMBER BCP 120-F; Taitec Corporation) and a small rotary shaker (NR-2; Taitec Corporation).

5. Removal of Surfactant

Each of the biological tissue samples was incubated in 30 ml of a 0.1 M borate buffer solution (pH 8.5) containing 0.1% by volume of Triton X-100 at 37° C. while shaking for 2 days.

6. Replacement of Solvent in Tissue (with Refractive Index-Homogenizing Solution)

Each of the biological tissue samples was incubated in ethylene glycol at room temperature for 10 minutes.

Figure 2:
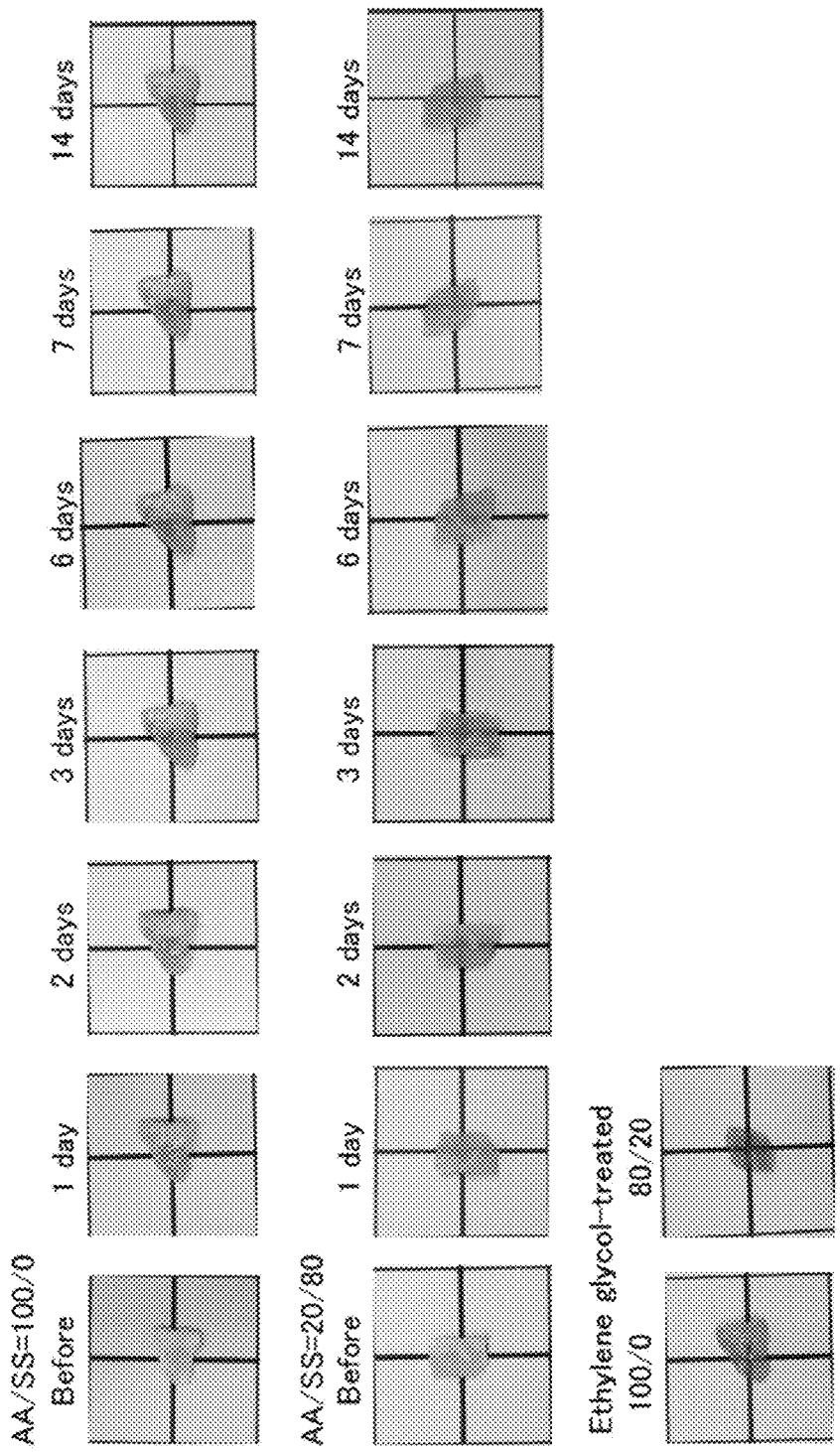
FIG. 2 illustrates photographs of biological tissue (cancer tissue) samples subjected to a conventional clearing method or another embodiment of the clearing method of the invention using sodium styrenesulfonate. In either method, lipids were removed by passive diffusion. The biological tissue samples are each placed on a grid board.

FIG. 2 shows the biological tissue samples before and during the delipidation (after 1, 2, 3, 6, 7 and 14 days of incubation), and after the solvent replacement. In the figure, the biological tissue samples are each placed on a 1-cm grid board.

As is clearly seen from FIG. 2, the biological tissue sample in which hydrogel had been formed from the monomers at a molar ratio of AA/SS=20/80 was becoming transparent after 1 or 2 days of delipidation and was fully transparent after 6 or 7 days of delipidation. Meanwhile, the biological tissue sample in which hydrogel had been formed from the monomers at a molar ratio of AA/SS=100/0 appeared to be finally becoming slightly transparent after 6 days of delipidation.

After 14 days of delipidation followed by replacement of the solvent in the tissue with ethylene glycol, the biological tissue samples in which hydrogels had been formed from the monomers were fully transparent regardless of the monomers used.

Evaluation of Physical Properties of AA/SS Copolymers (without any Crosslinking Agent)

Monomers (2.0 g, final concentration: 4.0 wt/vol %) at a molar ratio of AA/SS=100/0, 75/25, 50/50, 25/75 or 0/100 were dissolved in 1×PBS solution to prepare monomer solutions. In order to remove dissolved oxygen, nitrogen was bubbled through the monomer solutions under ice cooling for 5 minutes. In polymerization tubes, a polymerization initiator (VA-044; 0.25 wt/vol %) was then added to each of the monomer solutions and the polymerization was carried out at 37° C. for 24 hours.

The obtained polymer solutions were freeze-dried in 50-ml pear-shaped evaporating flasks for 16 hours (EYELA FDU-1200; Tokyo Rikakikai Co., Ltd.). Thereafter, each of the freeze-dried polymers was dissolved in 15 ml of distilled water. The polymers were each precipitated with 150 ml of methanol as a poor solvent at 50° C. and then separated from methanol using a membrane filter. Precipitation with ethanol at 60° C. and separation with a membrane filter were then carried out twice. Finally, ethanol was removed by vacuum drying to purify each of the polymers.

For a sample containing approximately 30 mg of each of the polymers in approximately 0.7 ml of deuterium water, $^1$H NMR spectrum was obtained on a nuclear magnetic resonator (ECS-400 and ECX-400; JEOL Ltd.).

For each of the polymers, the number average molecular weight and the molecular weight distribution was determined on a gel permeation chromatography system (co-2060, UV-2075Plus, RI-2031Plus and PU-2080Plus; JASCO Corporation) using TSKgel PWXL-CP as a column and a phosphate ($Na_2HPO_4$, $NaH_2PO_4$) buffer solution (pH 6.8) as a development solvent, at a flow rate of 0.5 ml/min and a temperature of 25° C. As a standard for calibration, PEO was used.

A 10 wt/wt % solution of each of the polymers in ethylene glycol was prepared. The refractive index of each of the solutions was determined with a multiple wavelength Abbe refractometer (DR-M2; Atago Co., Ltd.) at 21° C.

Results

Table 1 indicates the composition ratios (% by mole), yields, number average molecular weights (Mn), molecular weight distributions (Mw/Mn) and refractive indices of the five polymers formed from the monomers at molar ratios of AA/SS=100/0, 75/25, 50/50, 25/75 and 0/100.

The composition ratios in the polymers were almost equivalent to the composition ratios in the monomers used. This indicates that SS was incorporated into the resulting copolymer at the same composition ratio as that of the monomers used.

With increasing the SS ratio, the number average molecular weight decreases while the refractive index slightly increases.

TABLE 1

| sample | mol % in comonomer (AA/SS) | mol % in copolymer (AA/SS)[a] | yield (%) | $M_n$ | $M_w/M_n$ | refractive index |
|---|---|---|---|---|---|---|
| SS0 | 100/0 | 100/0 | 76 | $7.1 \times 10^4$ | 7.2 | 1.435 |
| SS25 | 75/25 | 74/26 | 86 | $1.3 \times 10^4$ | 5.4 | 1.437 |
| SS50 | 50/50 | 49/51 | 78 | $7.8 \times 10^3$ | 1.8 | 1.438 |
| SS75 | 25/75 | 20/80 | 76 | $7.4 \times 10^3$ | 4.5 | 1.438 |
| SS100 | 0/100 | 0/100 | 81 | $6.1 \times 10^3$ | 5.8 | 1.440 |

[a]Determined by $^1$H NMR spectra.

Evaluation of the Physical Properties of AA/SS Copolymer Hydrogel

Monomer solutions were prepared as follows.

Monomers (2.0 g, final concentration: 4.0 wt/vol %) at a molar ratio of AA/SS=100/0, 75/25, 50/50, 25/75, 15/85 or 0/100 and bisAA (final concentration: 0.050 wt/vol %) were dissolved in 1×PBS solution.

In order to remove dissolved oxygen, nitrogen was bubbled through the monomer solutions under ice cooling for 5 minutes and a polymerization initiator (VA-044; 0.25 wt/vol %) was then added to the monomer solutions.

The monomer solutions were placed in 100-ml beakers, which were then covered with cling film and placed in a thermostatic oven at 37° C. for 24 hours to form hydrogels.

The resulting hydrogels were soaked and washed in distilled water for 48 hours.

Measurement of Expansion Ratio

Small samples were cut off from the washed hydrogels, weighed and freeze-dried for 36 hours (EYELA FDU-1200; Tokyo Rikakikai Co., Ltd.), and then weighed again. The swelling ratios in water were calculated from the masses before and after drying, according to the following formula:

Swelling ratio (%)=([Wet mass]−[Dry mass])/[Dry mass]×100

Measurement of Gel Elastic Modulus

The dynamic viscoelasticities of the hydrogels were measured using a rheometer (HAAKE MARS III; EKO Instruments B.V.) with two sample plates both of which are parallel disks. The measurement conditions were: temperature: 37° C.; frequency co: 1 rad/min; hydrogel thickness: 5 mm.

The stress σ (Pa) and the storage modulus G' (Pa) were measured for sinusoidal strain γ (%). G' was given as an average of the values calculated in a strain range of 1 to 10% where no noise was generated on the stress response.

Results

Figure 3:
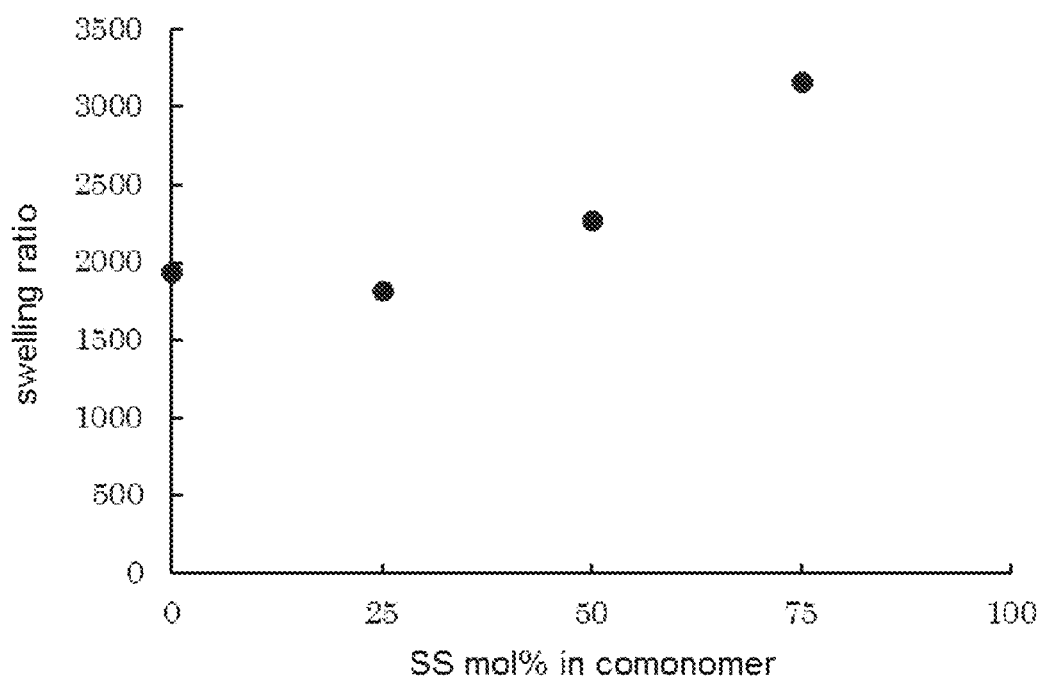
FIG. 3 illustrates swelling ratios of hydrogels comprised of a water-soluble ethylenically unsaturated monomer having an ionically dissociable group (sodium styrenesulfonate).
Figure 4:
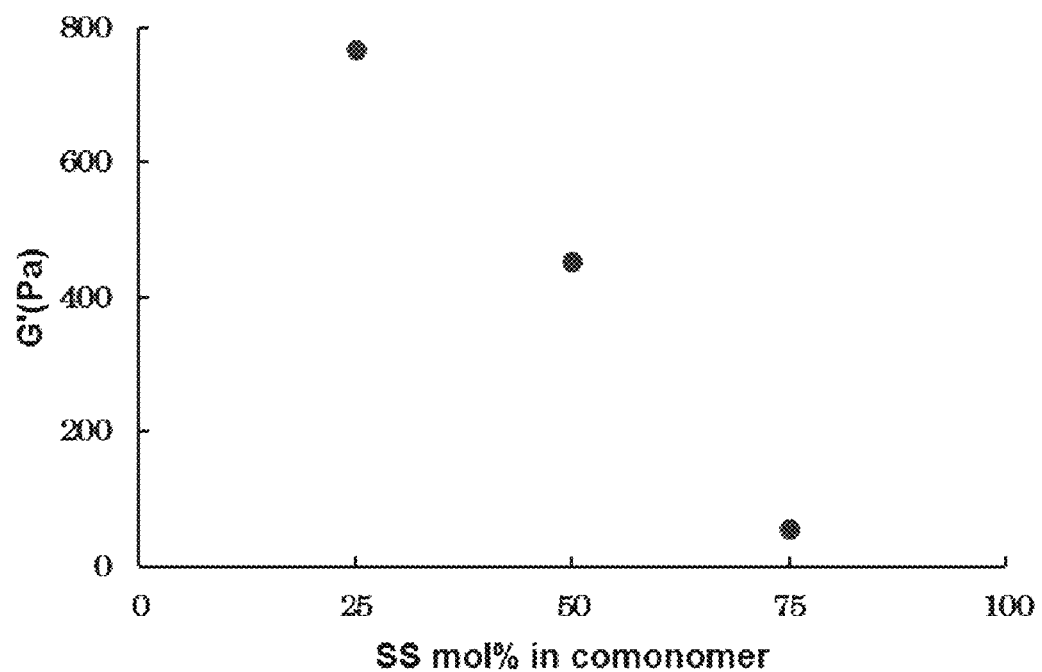
FIG. 4 illustrates elastic moduli of hydrogels comprised of a water-soluble ethylenically unsaturated monomer having an ionically dissociable group (sodium styrenesulfonate).

FIGS. 3 and 4 show the measured swelling ratios and elastic moduli, respectively, of the hydrogels.

The swelling ratio increases with an increase in SS ratio (molar ratio), and the highest swelling ratio was obtained with a molar ratio of AA/SS=75/25.

Meanwhile, the elastic modulus decreases with an increase in SS ratio (molar ratio), and the lowest elastic modulus was obtained with a molar ratio of AA/SS=25/75.

The results suggest that hydrogel formed from monomers at a higher SS ratio (molar ratio) has a large mesh size. It is deduced that such a large mesh size is attributed to charge repulsion between the ions (sulfonate ions in this case) in the hydrogel.

With the monomers at a molar ratio of 15/85 or 0/100 and the crosslinking agent at the concentration used (0.050 wt/vol %), no hydrogel was obtained that was rigid enough to maintain the structure of the delipidated biological tissue.

Biological Tissue Clearing (3)

Clearing Procedures

1. Preparation of Monomer Solution

A monomer solution containing a fixative was prepared as follows.

Monomers (0.4 g, final concentration: 4.0 wt/vol %) at a molar ratio of AA/AMPS=10/90, bisAA (final concentration: 0.050 wt/vol %), a polymerization initiator (VA-044; final concentration: 0.25 wt/vol %) and paraformaldehyde (final concentration: 4.0 wt/vol %) were dissolved in 10 mL of 1×PBS solution (pH 7.4).

2. Penetration of Monomers into Biological Tissue ("Infiltration Step")

In a 50-ml conical tube, a biological tissue sample (cancer tissue; approximately 0.4 cm×0.5 cm×0.07-0.08 cm) was immersed in the monomer solution at 4° C. for 1 day, thereby allowing the monomer solution to penetrate into the biological tissue sample.

3. Polymerization of Monomers ("Polymerization Step")

The conical tube was placed in a thermostatic oven at 37° C., thereby initiating polymerization reaction of the monomers infiltrated into the biological tissue sample. The polymerization reaction was carried out for 24 hours.

4. Delipidation ("Lipid Removal Step" or "Clearing Step")

The biological tissue sample was incubated in 30 ml of a 0.8 M borate buffer solution (pH 8.5) containing 4% (wt/vol) sodium lauryl sulfate at 37° C. while shaking using an incubator (BIO-CHAMBER BCP 120-F; Taitec Corporation) and a small rotary shaker (NR-2; Taitec Corporation).

5. Removal of Surfactant

The biological tissue sample was incubated in 30 ml of a 0.1 M borate buffer solution (pH 8.5) containing 0.1% by volume of Triton X-100 at 37° C. while shaking for 2 days.

Results

Figure 5:
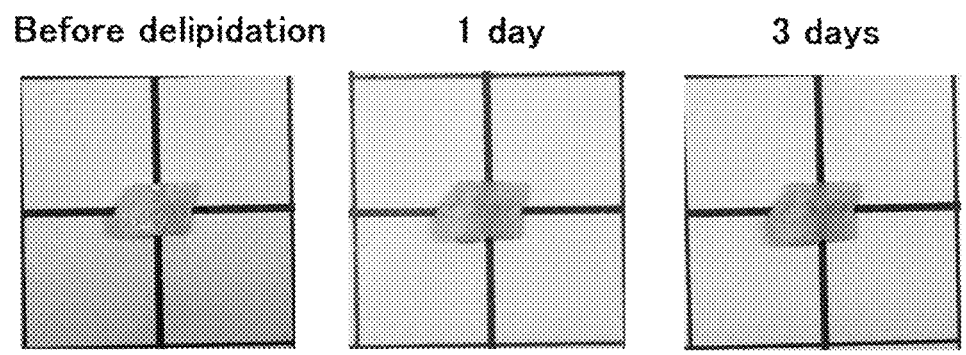
FIG. 5 illustrates photographs of a biological tissue (cancer tissue) sample subjected to one embodiment of the clearing method of the invention using sodium 2-acrylamido-2-methylpropanesulfonate, wherein lipids were removed by passive diffusion. The biological tissue sample is placed on a grid board.

FIG. 5 shows the biological tissue sample before and during the delipidation (after 1 and 3 days of incubation). In the figure, the biological tissue sample is placed on a 1-cm grid board.

As is clearly seen from FIG. 5, the biological tissue sample in which hydrogel had been formed from the monomers at a molar ratio of AA/AMPS=10/90 was becoming transparent after 1 to 3 days of delipidation. With monomers at a molar ratio of 0/100 and the crosslinking agent at the concentration used (0.050 wt/vol %), no hydrogel was obtained that was rigid enough to maintain the structure of the delipidated biological tissue.

Biological Tissue Clearing (4)

Clearing Procedures

1. Preparation of Monomer Solution

A monomer solution containing a fixative was prepared as follows.

An acrylic acid monomer (0.4 g, final concentration: 4.0 wt/vol %), bisAA (final concentration: 0.050 wt/vol %), a polymerization initiator (VA-044; final concentration: 0.25 wt/vol %) and paraformaldehyde (final concentration: 4.0 wt/vol %) were dissolved in 10 mL of 1×PBS solution (pH 7.4).

2. Penetration of Monomers into Biological Tissue ("Infiltration Step")

In a 50-ml conical tubes, a biological tissue sample (cancer tissue; approximately 0.5 cm×0.5 cm×0.07-0.08 cm) was immersed in the monomer solution at 4° C. for 1 day, thereby allowing the monomer solution to penetrate into the biological tissue sample.

3. Polymerization of Monomer ("Polymerization Step")

The conical tube was placed in a thermostatic oven at 37° C., thereby initiating polymerization reaction of the monomers infiltrated into the biological tissue sample. The polymerization reaction was carried out for 24 hours.

4. Delipidation ("Lipid Removal Step" or "Clearing Step")

The biological tissue sample was incubated in 30 ml of a 0.8 M borate buffer solution (pH 8.5) containing 4% (wt/vol) sodium lauryl sulfate at 37° C. while shaking using an incubator (BIO-CHAMBER BCP 120-F; Taitec Corporation) and a small rotary shaker (NR-2; Taitec Corporation).

5. Removal of Surfactant

The biological tissue sample was incubated in 30 ml of a 0.1 M borate buffer solution (pH 8.5) containing 0.1% by volume of Triton X-100 at 37° C. while shaking for 2 days.

Results

Figure 6:
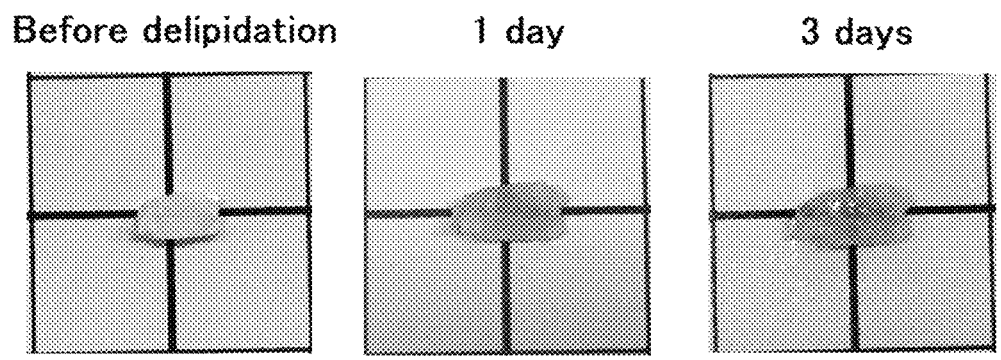
FIG. 6 illustrates photographs of a biological tissue (cancer tissue) sample subjected to one embodiment of the clearing method of the invention using acrylic acid, wherein lipids were removed by passive diffusion. The biological tissue sample is placed on a grid board.

FIG. 6 shows the biological tissue sample before and during the delipidation (after 1 and 3 days of incubation). In the figure, the biological tissue sample is placed on a 1-cm grid board.

As is clearly seen from FIG. 6, the biological tissue sample in which hydrogel had been formed from acrylic acid monomer was becoming transparent after 1 to 3 days of delipidation.

Biological Tissue Clearing (5)

Clearing Procedures

1. Preparation of Monomer Solutions

A monomer solution containing a fixative was prepared as follows.

Monomers (final concentration: 0.56 M) at a molar ratio of AA/AcA=25/75, bisAA (final concentration: 0.050 wt/vol %), a polymerization initiator (VA-044; final concentration: 1.25 wt/vol %) and paraformaldehyde (final concentration: 4.0 wt/vol %) were dissolved in 10 mL of 1×PBS solution (pH 7.4).

2. Penetration of Monomers into Biological Tissue ("Infiltration Step")

In 50-ml conical tubes, biological tissue samples (cancer tissues; approximately 0.4 cm×0.5 cm×0.07 cm) were immersed in the respective monomer solutions at 4° C. for 1 day, thereby allowing the monomer solutions to penetrate into the biological tissue samples.

3. Polymerization of Monomers ("Polymerization Step")

The conical tubes were placed in a thermostatic oven at 37° C., thereby initiating polymerization reaction of the monomers infiltrated into the biological tissue samples. The polymerization reaction was carried out for 24 hours.

4. Delipidation ("Lipid Removal Step" or "Clearing Step")

Each of the biological tissue samples was incubated in 30 ml of a 0.8 M borate buffer solution (pH 8.5) containing 4% (wt/vol) sodium lauryl sulfate at 37° C. while shaking using an incubator (BIO-CHAMBER BCP 120-F; Taitec Corporation) and a small rotary shaker (NR-2; Taitec Corporation) for 1 day or 3 days.

5. Removal of Surfactant

Each of the biological tissue samples was incubated in 30 ml of a 0.1 M borate buffer solution (pH 8.5) containing 0.1% by volume of Triton X-100 at 37° C. while shaking for 2 days.

6. Replacement of Solvent in Tissue (with Refractive Index-Homogenizing Solution)

Each of the tissue samples, from which sodium lauryl sulfate had been removed, was immersed for 1 hour in ethylene glycol (refractive index: 1.42), which substituted for the solvent in the tissue samples.

After the replacement with ethylene glycol, the tissue samples were visually evaluated for transparency using a 1-cm grid board.

Results

Figure 7:
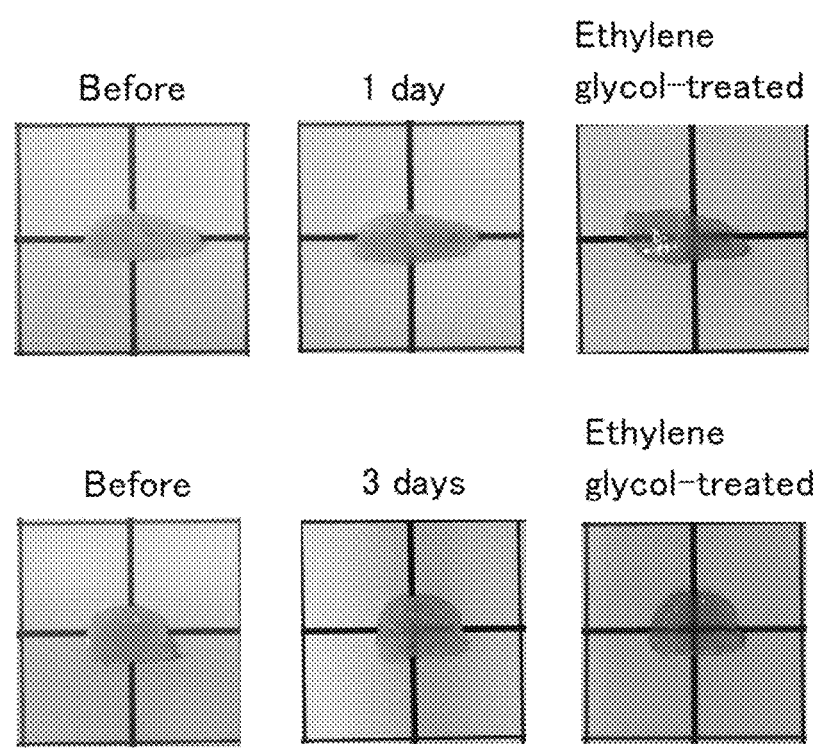
FIG. 7 illustrates photographs of biological tissue (cancer tissue) samples subjected to another embodiment of the clearing method of the invention using acrylic acid (AcA75).

FIG. 7 shows the cancer tissue samples before and during the delipidation (after 1 and 3 days of delipidation), and after the replacement with ethylene glycol.

As is clearly seen from FIG. 7, the biological tissue samples, in which hydrogel had been formed from the monomers at a molar ratio of AA/AcA=25/75, were becoming transparent after 1 day of delipidation and were more transparent after 3 days of delipidation. The replacement with ethylene glycol rendered the samples further more transparent. The results confirm that the present method can use an acrylic acid (AcA) monomer in combination with an acrylamide (AA) monomer (meaning that the present method works also by forming an AA/AcA copolymer gel in biological tissues).

Biological Tissue Clearing (6)

1. Preparation of Monomer Solutions

Monomer solutions containing a fixative were prepared as follows.

An AA monomer or monomers at a molar ratio of AA/AcA=25/75 (final concentration: 0.56 M), bisAA (final concentration: 0.050 wt/vol %), a polymerization initiator (VA-044; final concentration: 1.25 wt/vol %) and paraformaldehyde (final concentration: 4.0 wt/vol %) were dissolved in 10 mL of 1×PBS solution (pH 7.4).

2. Penetration of Monomers into Biological Tissue ("Infiltration Step")

In 50-ml conical tubes, biological tissue samples (cancer tissues; approximately 0.4 cm×0.5 cm×0.07 cm) were immersed in the respective monomer solutions at 4° C. for 1 day, thereby allowing the monomer solutions to penetrate in the biological tissue samples.

3. Polymerization of Monomers ("Polymerization Step")

The conical tubes were placed in a thermostatic oven at 37° C., thereby initiating polymerization reaction of the monomers infiltrated into the biological tissue samples. The polymerization reaction was carried out for 24 hours.

4. Delipidation ("Lipid Removal Step" or "Clearing Step")

Each of the biological tissue samples was incubated in 30 ml of a 0.8 M borate buffer solution (pH 8.5) containing 4% (wt/vol) sodium lauryl sulfate at 37° C. while shaking using an incubator (BIO-CHAMBER BCP 120-F; Taitec Corporation) and a small rotary shaker (NR-2; Taitec Corporation) for 3 days.

5. Removal of Surfactant

Each of the biological tissue samples was incubated in 30 ml of a 0.1 M borate buffer solution (pH 8.5) containing 0.1% by volume of Triton X-100 at 37° C. while shaking for 1 day.

6. Immunofluorescent Staining

Each of the tissue samples was placed in a PBST solution (30 ml), which was a PBS solution containing Tween 20 (0.050 wt %) added thereto, and shaken for 1 hour.

Thereafter, each of the tissue samples was incubated with a fluorescently-labeled antibody (Monoclonal Anti-Actin, α-Smooth Muscle (αSMA antibody)-FITC antibody) diluted to 1:100 in a PBST solution at 37° C. for 1 day while shaking.

The tissue samples were then washed in 50 ml of a PBS solution while shaking for a total of 1 day, during which the PBS solution was exchanged 4 times.

7. Replacement of Solvent in Tissue (with Refractive Index-Homogenizing Solution)

The tissue samples were immersed in ethylene glycol for 1 hour and then observed for fluorescence with an inverted research microscope Ti-U (Nikon).

Results

Figure 8:
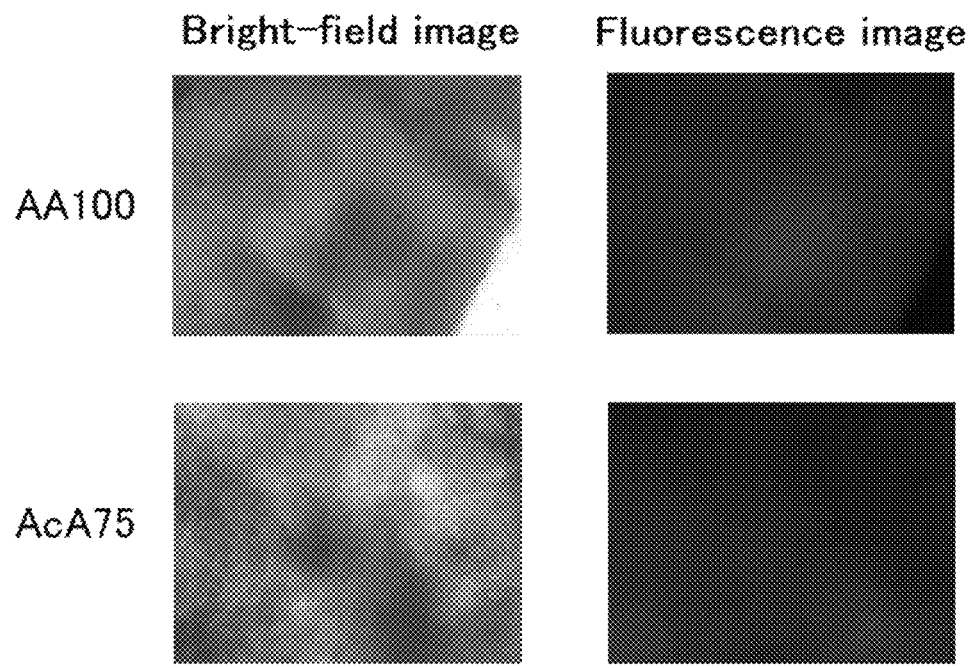
FIG. 8 illustrates fluorescent micrographs of biological tissue (cancer tissue) samples subjected to a conventional clearing method (AA100) or another embodiment of the clearing method of the invention using acrylic acid (AcA75), followed by immunostaining.

FIG. 8 shows micrographs of immunostained cancer tissue samples. The αSMA antibody is known to stain vascular endothelial cells. Fluorescence due to the αSMA antibody was observed in both of the tissue samples (AA alone and AcA75).

Biological Tissue Clearing (7)

Brain tissue samples (3 mm×2 mm×1 mm) from GFP-expressing mouse were cleared according to the same procedures as described in "Biological tissue clearing (5)" above. The delipidation was carried out for 3 days.

As a comparison, the clearing study was conducted also according to a conventional method using the same procedures except for the replacement of the monomers at a molar ratio of AA/AcA=25/75 with the monomers at a molar ratio of AA/AcA=100/0.

Figure 9:
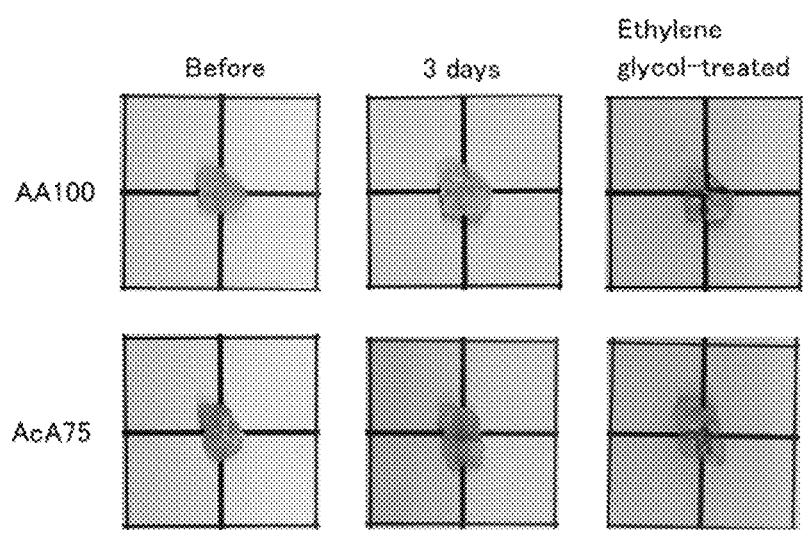
FIG. 9 illustrates photographs of biological tissue (brain tissue) samples subjected to a conventional clearing method (AA100) or one embodiment of the clearing method of the invention (AcA75).

FIG. 9 shows the brain tissue samples (on 1-cm grid boards) before and after the delipidation and also after the replacement with ethylene glycol. The sample cleared by the conventional method ("AA100") was transparent at the same level as the sample cleared by the present method ("AcA75"). This is because brain tissues are easy to be cleared.

Figure 10:
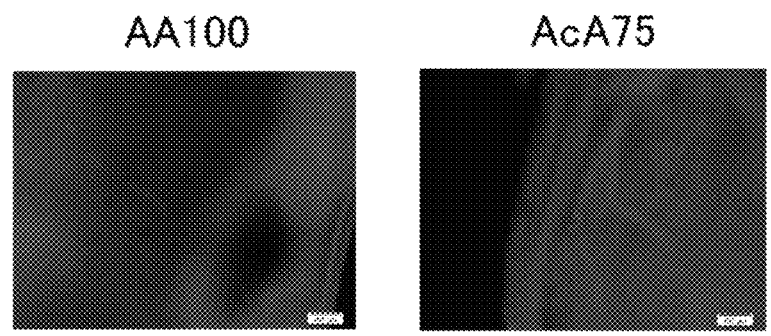
FIG. 10 illustrates fluorescent micrographs of GFP-expressing mouse brain tissue samples subjected to a conventional clearing method (AA100) or an embodiment of the clearing method of the invention (AcA75).

In cell culture petri dishes, the GFP-containing tissue samples after the ethylene glycol replacement were observed for GFP fluorescence with an inverted fluorescence microscope (Olympus, IX-71) (FIG. 10).

It was observed that the fluorescent intensity of the tissue sample cleared by the present method ("AcA75") was comparable to that of the tissue sample cleared by the conventional method ("AA100"). This confirms that fluorescence imaging is feasible in tissue samples cleared according to the present method.

Evaluation of Physical Properties of AA/AcA Copolymer Hydrogel

The monomer solution prepared was a 10 mL PBS solution (pH 7.4) containing monomers (final concentration: 0.56 M) at a molar ratio of AA/AcA=25/75 and bisAA (final concentration: 0.050 wt %).

In order to remove dissolved oxygen, nitrogen was bubbled through the monomer solution under ice cooling for 5 minutes and a polymerization initiator (VA-044; 0.25 wt/vol %) was then added to the solution.

The resulting monomer solution was placed in a 100-ml beaker, which was then covered with cling film. Polymerization was carried out at 37° C. for 3, 6 or 12 hours to form hydrogels.

The formed hydrogels were soaked and washed in distilled water for 48 hours.

Small samples were cut off from the washed hydrogels, weighed and freeze-dried for 36 hours (EYELA FDU-1200; Tokyo Rikakikai Co., Ltd.), and then weighed again. The swelling ratios in water were calculated from the masses before and after drying, according to the following formula:

$$\text{Swelling ratio (\%)} = ([\text{Wet mass}] - [\text{Dry mass}])/[\text{Dry mass}] \times 100$$

Figure 11:
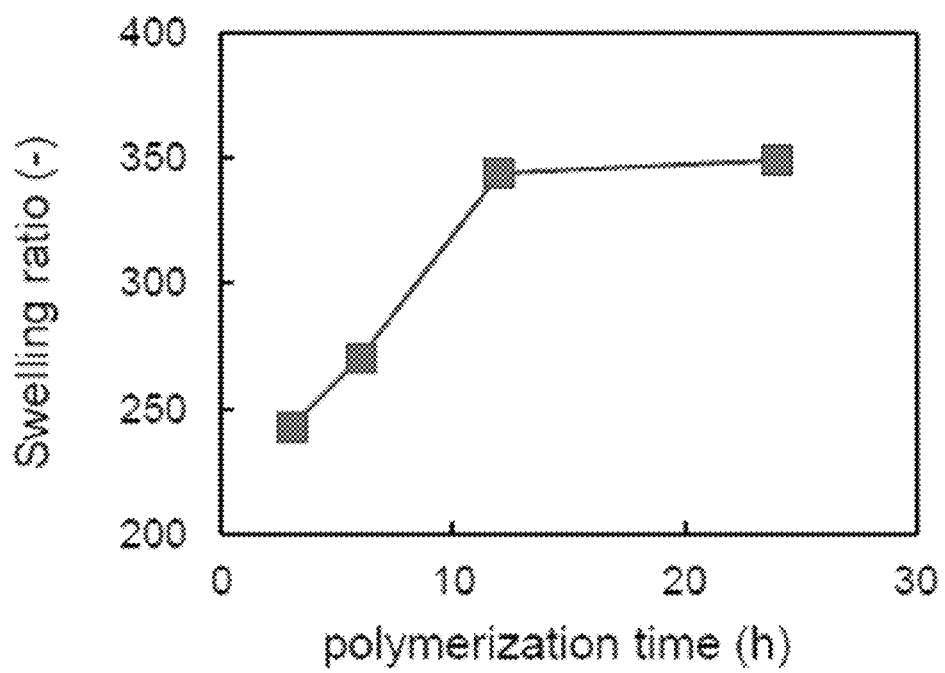
FIG. 11 illustrates swelling ratios of AA/AcA copolymer hydrogels formed for different polymerization times.

FIG. 11 indicates the measured swelling ratios of the AA/AcA copolymer hydrogels (AA/AcA=25/75). As indicated in the figure, the swelling ratio increased until 12 hours after initiating the polymerization, and was flat thereafter.

Biological Tissue Clearing (8)

Cancer tissue samples were cleared in the same manner as described in "Biological tissue clearing (5)" above except that polymerization reaction was carried out for 3, 6, 12 or 24 hours and the delipidation was carried out for 3 days.

Figure 12:
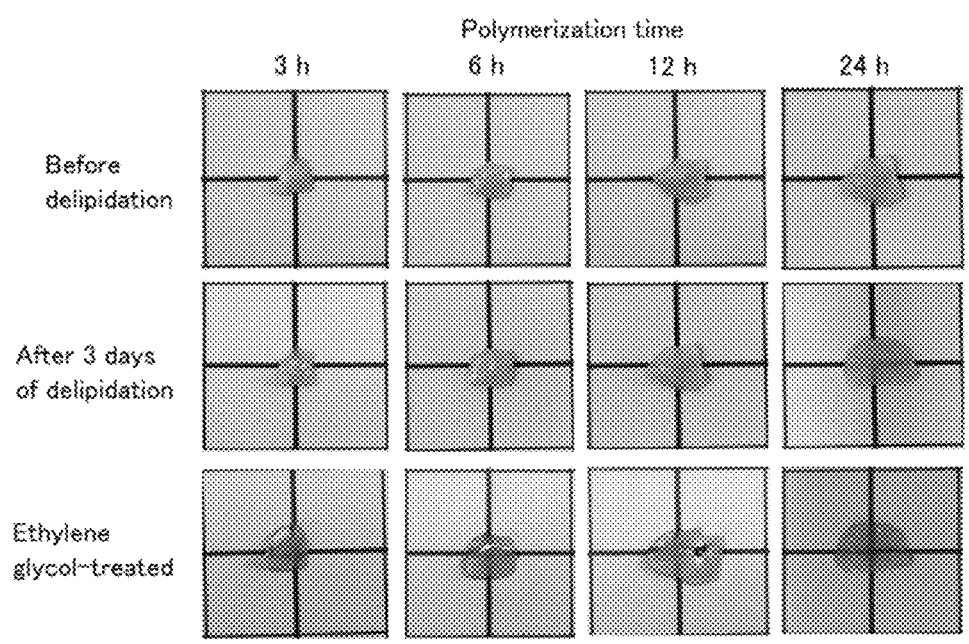
FIG. 12 illustrates photographs of biological tissue (cancer tissue) samples subjected to different embodiments (polymerization time: 3, 6, 12 and 24 hours) of the clearing method of the invention.

FIG. 12 shows the cancer tissue samples before delipidation, after 3 days of delipidation and after replacement with ethylene glycol. The results confirm that the method using 12 hours of polymerization could achieve a comparable level of tissue transparency to that achieved by the method using 24 hours of polymerization.

As is clearly seen from the results mentioned above, the present method using a monomer having an ionically dissociable group as a monomer unit forming a hydrogel can achieve tissue clearing in a short time and the cleared tissues may be used for immunostaining and fluorescent protein observation The rapid tissue clearing provided by the method of the invention may result from a large hydrogel mesh size, which is attributed to charge repulsion between the ionically dissociable groups in the gel. In addition, high refractive index of the copolymer may contribute to the tissue clearing.

The invention claimed is:

1. A method for clearing a biological tissue, comprising the steps of:
   infiltrating the biological tissue with water-soluble ethylenically unsaturated monomers before, during or after fixing the biological tissue with a fixative, wherein the water-soluble ethylenically unsaturated monomers comprise at least a water-soluble ethylenically unsaturated monomer having an ionically dissociable group;
   polymerizing the water-soluble ethylenically unsaturated monomers to form a hydrogel in the fixed biological tissue; and
   removing a lipid from the fixed biological tissue,
   wherein the water-soluble ethylenically unsaturated monomers comprise at least 50% by mole of the water-soluble ethylenically unsaturated monomer having an ionically dissociable group.

2. The method according to claim 1, wherein the ionically dissociable group is an anionically dissociable group.

3. The method according to claim 1, wherein the ionically dissociable group is a sulfonate, carbonate or phosphate group.

4. The method according to claim 1, wherein the water-soluble ethylenically unsaturated monomer having an ionically dissociable group is selected from (meth)acrylic acid, itaconic acid, maleic acid, fumaric acid and salts thereof.

5. The method according to claim 1, wherein the water-soluble ethylenically unsaturated monomer having an ionically dissociable group is selected from styrenesulfonic acid, (meth)acryloxybenzenesulfonic acid, 2-(meth)acrylamido-2-methylpropanesulfonic acid, 2-(meth)acrylamidopropanesulfonic acid, 3-(meth)acrylamido-2-hydroxypropanesulfonic acid, 3-(meth)acryloxy-1-propanesulfonic acid and salts thereof.

6. The method according to claim 1, wherein the water-soluble ethylenically unsaturated monomers comprise a (meth)acrylamide-based monomer.

7. The method according to claim 1, wherein the lipid removal is by passive diffusion.

8. A method for preparing a preparation of a cleared biological tissue, comprising applying the method according to claim 1 to a biological tissue, and treating the cleared biological tissue with a preservative.

9. The method according to claim 2, wherein the water-soluble ethylenically unsaturated monomers comprise a (meth)acrylamide-based monomer.

10. The method according to claim 4, wherein the water-soluble ethylenically unsaturated monomers comprise a (meth)acrylamide-based monomer.

11. The method according claim 5, wherein the lipid removal is by passive diffusion.

12. The method according to claim 3, wherein the lipid removal is by passive diffusion.

13. The method according to claim 2, wherein the lipid removal is by passive diffusion.

14. The method according to claim 6, wherein the lipid removal is by passive diffusion.

15. The method according to claim 9, wherein the lipid removal is by passive diffusion.

16. The method according to claim 10, wherein the lipid removal is by passive diffusion.

17. The method according to claim 1, wherein the water-soluble ethylenically unsaturated monomer having an ionically dissociable group is selected from (meth)acrylic acid, styrenesulfonic acid, 2-(meth)acrylamido-2-methylpropanesulfonic acid and salts thereof, and wherein the lipid removal is by passive diffusion.

18. The method according to claim 1, wherein the water-soluble ethylenically unsaturated monomer having an ionically dissociable group is selected from styrenesulfonic acid, 2-(meth)acrylamido-2-methylpropanesulfonic acid and salts thereof, and wherein the lipid removal is by passive diffusion.

19. The method according to claim 1, wherein the water-soluble ethylenically unsaturated monomers comprise at least 60% by mole of the water-soluble ethylenically unsaturated monomer having an ionically dissociable group.

20. The method according to claim 1, wherein the water-soluble ethylenically unsaturated monomers comprise at least 70% by mole of the water-soluble ethylenically unsaturated monomer having an ionically dissociable group.

* * * * *